United States Patent [19]
Audeh et al.

[11] Patent Number: 5,463,168
[45] Date of Patent: Oct. 31, 1995

[54] PROCESS FOR THE REMOVAL OF HYDROGEN CYANIDE FROM FCC HYDROCARBON PRODUCT GAS STREAMS

[75] Inventors: Costandi A. Audeh, Sun City West, Ariz.; David S. Shihabi, Pennington, N.J.; Richard F. Socha, Newtown; Scott A. Stevenson, Langhorne, both of Pa.

[73] Assignee: Mobil Oil Corporation, Fairfax, Va.

[21] Appl. No.: 291,802

[22] Filed: Aug. 17, 1994

[51] Int. Cl.$^6$ .............................. C07C 7/00; C01C 3/00; B01J 8/00

[52] U.S. Cl. .......................... 585/854; 585/855; 423/236; 423/239.1

[58] Field of Search ..................... 585/854, 855; 423/236, 239.1

[56] References Cited

U.S. PATENT DOCUMENTS

| | | | |
|---|---|---|---|
| 2,239,000 | 4/1941 | Groombridge et al. | 252/373 |
| 2,243,689 | 7/1947 | Day | 252/192 |
| 3,441,370 | 4/1969 | Gutmann et al. | 23/2 |
| 3,492,083 | 1/1970 | Lowicki et al. | 23/2 |
| 4,009,009 | 2/1977 | Massoth et al. | 55/73 |
| 4,128,619 | 12/1978 | Robinson | 423/244 |
| 4,271,133 | 6/1981 | Tellis | 423/230 |
| 4,275,049 | 6/1981 | Voigt et al. | 423/352 |
| 5,173,278 | 12/1992 | Marler et al. | 423/239 |

FOREIGN PATENT DOCUMENTS 2650711 6/1977 Germany.

Primary Examiner—Anthony McFarland
Assistant Examiner—Nhat D. Phan
Attorney, Agent, or Firm—Alexander J. McKillop; Malcolm D. Keen; Charles A. Malone

[57] ABSTRACT

A process is described wherein the HCN in FCC hydrocarbon gas streams is converted to NH$_3$ over a catalyst. This conversion has the desirable result of decreasing the amount of CN$^-$ in the water leaving the sour-water stripper, and ultimately in the refinery water effluent.

20 Claims, 2 Drawing Sheets

PROCESS FOR THE REMOVAL OF HYDROGEN CYANIDE FROM FCC HYDROCARBON PRODUCT GAS STREAMS

FIELD OF THE INVENTION

This invention relates to the removal of hydrogen cyanide from gaseous process streams. More particularly, it relates to the treatment of such process streams with adsorbent beds containing vanadium and titanium to reduce the hydrogen cyanide content of such streams to very low levels of concentration.

BACKGROUND OF THE INVENTION

Synthesis gas is an increasingly important feedstock in the chemical industry. Existing or proposed commercial processes using synthesis gas (i.e. gaseous mixtures containing hydrogen and carbon monoxide) include processes for the manufacture of methanol, ethanol, the production of aldehydes by the oxo process, the production of glycols using rhodium catalysts, and the production of purified hydrogen and carbon monoxide streams. In most of these processes, the use of sensitive catalyst materials requires that contaminants such as sulfur compounds and hydrogen cyanide be removed from the gas to concentration levels of less than 1 part per million, by volume (hereinafter referred to as "ppmv",) and often to levels below 0.1 ppmv.

Synthesis gas mixtures typically contain a variety of impurities among which are sulfur compounds such as hydrogen sulfide ($H_2S$), carbonyl sulfide (COS), sulfur dioxide ($SO_2$) carbon disulfide ($CS_2$) and methyl mercaptan ($CH_3SH$) as well as hydrogen cyanide (HCN), hydrogen chloride (HCl) and others. The relative concentrations of these impurities in the gas depends on the feedstock from which the synthesis gas is derived. Generally, a gaseous feedstock, such as methane, introduces less contaminants into the synthesis gas than liquid feedstocks, such as naphtha, gas oil, atmospheric residue (the bottom fraction obtained from an atmospheric crude refining still) and vacuum residue (the bottom fraction obtained from the vacuum refining of heavy feedstocks such as crude oil and atmospheric residue). Coal derived synthesis gases generally contain the highest concentration os sulfur compounds.

Present purification schemes typically utilize a reactive liquid absorbent such as aqueous ethanolamines, alkali carbonates and hydroxides, or sodium thioarsenite as a primary purification agent to absorb high levels of the various species of impurities and generally reduce them to levels of about 1 to 10 ppmv. Alternatively, a non-reactive physical absorbent such as methanol at cryogenic temperatures may be used as the primary purification agent. Purifying the gaseous stream to a higher degree with such adsorbents is uneconomical because of the disproportionately large amounts of energy which would be required to regenerate the spent absorbent.

Accordingly, the effluent gas from a primary purification step usually requires further treatment to reduce the impurities to acceptable levels. Adsorbents to accomplish such purification are extensively described in the prior art. The prior art literature relating to adsorbents for gaseous purification concerns itself, for the most part, with eliminating sulfur compounds from gas streams, in particular $H_2S$. Thus, for example, U.S. Pat. No. 3,441,370 describes the removal of $H_2S$ with the use of a zinc oxide adsorbent at a temperature from ambient to 800° F. The removal of COS and RSH is also suggested, but only at temperatures about 500° F. However, no data are provided in the patent to support this suggestion. U.S. Pat. No. 4,009,009 describes the removal of COS from arsenic-free gas streams with the use of alumina-supported lead oxide. Great Britain Application No. 012,540, filed Mar. 29, 1976 (corresponding to German Offenlegungshrift 2,650,711 published Jun. 10, 1977) discloses the use of zinc oxide as an absorbent for hydrogen sulfide. The examples of the application show the removal of carbonyl sulfide along with $H_2S$, but the presence of carbonyl sulfide in the inlet feed gas is said to be restricted to small amounts (page 4, col. 2).

U.S. Pat. No. 3,492,083 broadly describes the removal of $H_2S$ and COS from an industrial gas using as an adsorbent a mixture comprising oxides of aluminum, zinc, iron and/or manganese in combination with oxides of the alkaline earth and/or alkali metals. Adsorption is carried out at a temperature of from 100° to 300° C. The examples of the patent only disclose the removal of $H_2S$ and $SO_2$ from the various gases. U.S. Pat. No. 4,128,619 discloses a desulfurization process carried out at a temperature from 100°–400° C. using zinc oxide as the adsorbent. Hydrogen sulfide is the only sulfur compound which is shown removed in the examples of the patent. U.S. Pat. No. 2,239,000 discloses the removal of sulfur from gas mixtures comprising hydrogen and carbon monoxide at a temperature from 400° C.–600° C. using catalytic mixtures of zinc and iron oxides or zinc and chromium oxides.

The removal of hydrogen cyanide from a gas stream using soda lime as an adsorbent is disclosed in U.S. Pat. No. 2,423,689. The addition of up to 10 percent by weight of zinc oxide to the soda lime is suggested for purposes of increasing the life and hardness of the soda lime.

Thus, while zinc oxide is generally known in the prior art as an adsorbent for the removal of sulfur compounds, such as, $H_2S$ and $CH_3SH$, there has heretofore been no appreciation regarding its capability as an adsorbent for HCN.

U.S. Pat. No. 4,271,133 which issued to Tellis on Jun. 2, 1981 teaches a process for reducing the hydrogen cyanide content of a gaseous stream which comprises providing an adsorbent bed wherein the adsorbent comprises zinc oxide and contains about 5 wt. % of an oxide of an alkali or alkaline earth metal, and contacting said process stream with the adsorbent bed at a temperature of from about ambient to about 350 degrees C. for a period of time sufficient to reduce the concentration of the hydrogen cyanide.

Voigt et al. in U.S. Pat. No. 4,275,049 disclose a catalytic process for converting hydrogen cyanide into ammonia where a special iridium catalyst is utilized in the presence of an equivalent amount of hydrogen to obtain the transformation.

Thus, while the above adsorbents and catalysts have been used to convert hydrogen cyanide to ammonia, there is no suggestion to use $MgO/SiO_2$, $SnO_2$, $Li_2O/SiO_2$ or vanadia/titania catalysts to make a similar conversion. Therefore, what is needed is a process to convert hydrogen cyanide to ammonia by contacting a gaseous stream containing said hydrogen cyanide with these novel catalysts.

SUMMARY OF THE INVENTION

In the practice of this invention, a hydrocarbonaceous gas stream containing hydrogen cyanide e.g. from a main distillation unit fluidly connected to a Fluid Catalytic Cracking (FCC) unit is contacted with a selective reduction catalyst bed. Said hydrocarbonaceous gas stream is preferably contacted with a catalyst bed at a temperature of from about 150° C. to about 500° C. for a period of time sufficient to reduce the content of hydrogen cyanide in the gaseous stream to a desired concentration.

This invention is predicated on the discovery that a catalyst selected from a member of the group consisting of $MgO/SiO_2$, $SnO_2$, $Li_2O/SiO_2$, or vanadia/titania is an effective catalyst for HCN conversion, and that it can be used to remove such impurity from gaseous process streams at commercially practical temperatures and space velocities to concentrations below detectable limits of HCN in such gaseous stream, namely, a concentration in the range of 5–10 parts per billion, by volume (ppbv).

Upon contact with the catalyst, HCN contained in the gaseous stream is converted to $NH_3$. The produced ammonia is then concentrated in an accumulator and subsequently directed therefrom into contact with water, e.g. water contained in a sour water stripper, where it is absorbed therein. Water containing the ammonia is combined with other refinery waste water streams and disposed of.

It is therefore an object of this invention to convert HCN contained in a gaseous stream to $NH_3$ via a catalyst selected from a member of the group consisting of $MgO/SiO_2$, $SnO_2$, $Li_2O$, and vanadia/titania or other suitable materials.

It is another object of this invention to avoid environmental problems resultant from the disposal of harmful concentrations of HCN contained in refinery waste water streams.

It is a further object of this invention to remove HCN from a refinery gaseous stream catalytically while avoiding polymerization of olefinic compounds contained in said stream.

DESCRIPTION OF THE PREFERRED EMBODIMENTS

Figure 1:
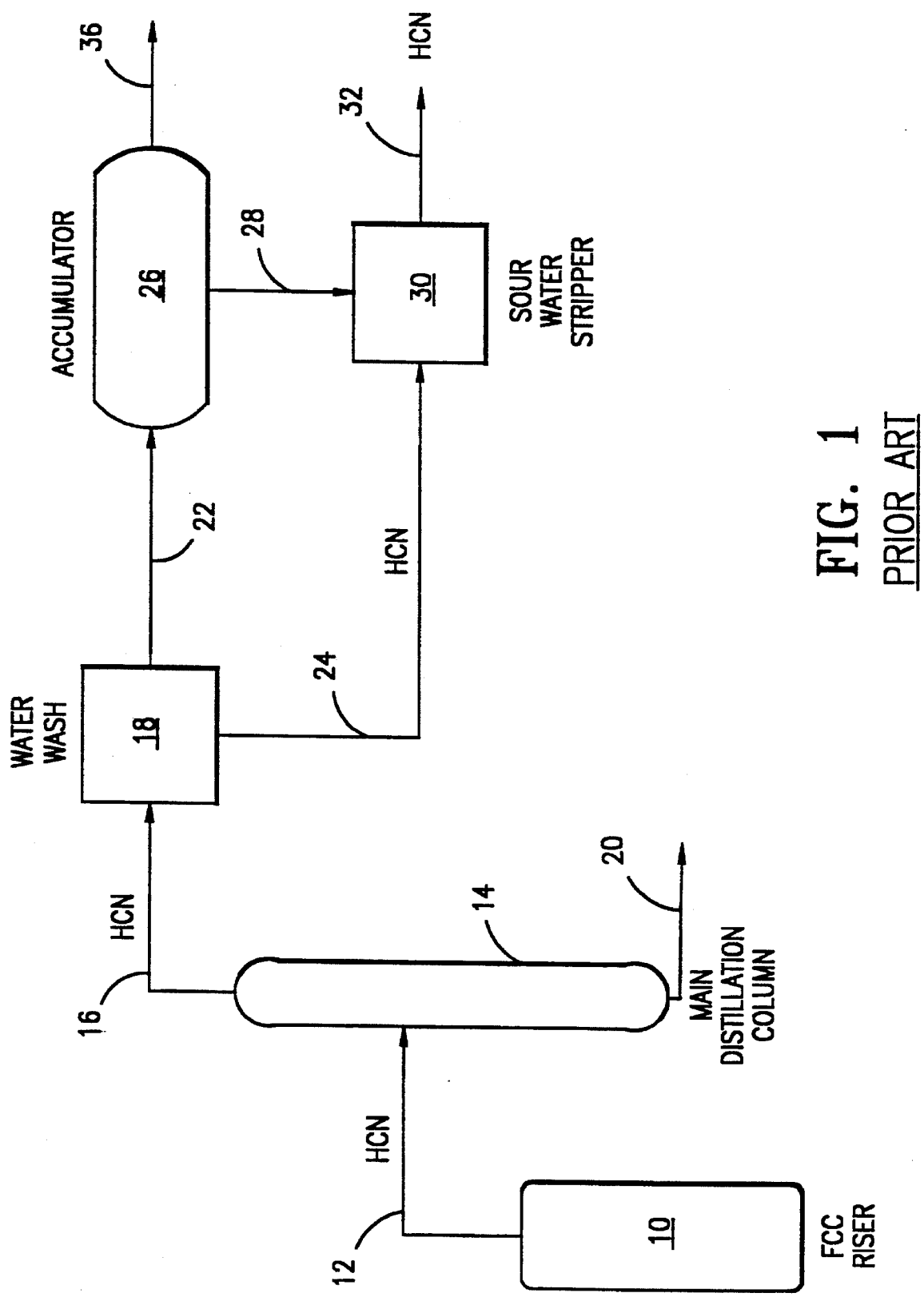
FIG. 1 is a block diagram of a prior art refinery scheme for the removal of HCN from a FCC riser gaseous stream containing HCN.

As is shown in FIG. 1, the conventional method for removing HCN from overhead from a FCC riser column 10 is to direct the overhead hydrocarbonaceous gas stream via conduit 12 into main distillation column 14. This gas stream contains in addition to HCN, lower boiling point hydrocarbons e.g. $C_1$ to $C_4$, hydrogen sulfide, sulfur dioxide, and carbon disulfide. Higher boiling point hydrocarbons are removed from main distillation column 14 via conduit 20 while lower boiling point components including HCN are removed from column 14 via conduit 16. Conduit 16 directs these lower boiling components including HCN into water wash 18 where the $CN^-$ ions are absorbed into the water. This water containing the $CN^-$ ions is removed from water wash 18 via conduit 24 and directed into sour water stripper 30. Unabsorbed gases are removed from water wash 18 via conduit 22 and feed into accumulator 26 where additional entrained water is separated from the gas. Separated water from the accumulator is removed therefrom by conduit 28 into sour water stripper 30 where it is combined with the wash water from vessel 18. Substantially $CN^-$ free gas is removed from accumulator 26 via conduit 36 where it is utilized in the refinery operations or flared. Water containing $CN^-$ ions is removed from sour water stripper 30 via conduit 32 and sent to a disposal unit to reduce the cyanide concentration to environmentally acceptable levels.

Figure 2:
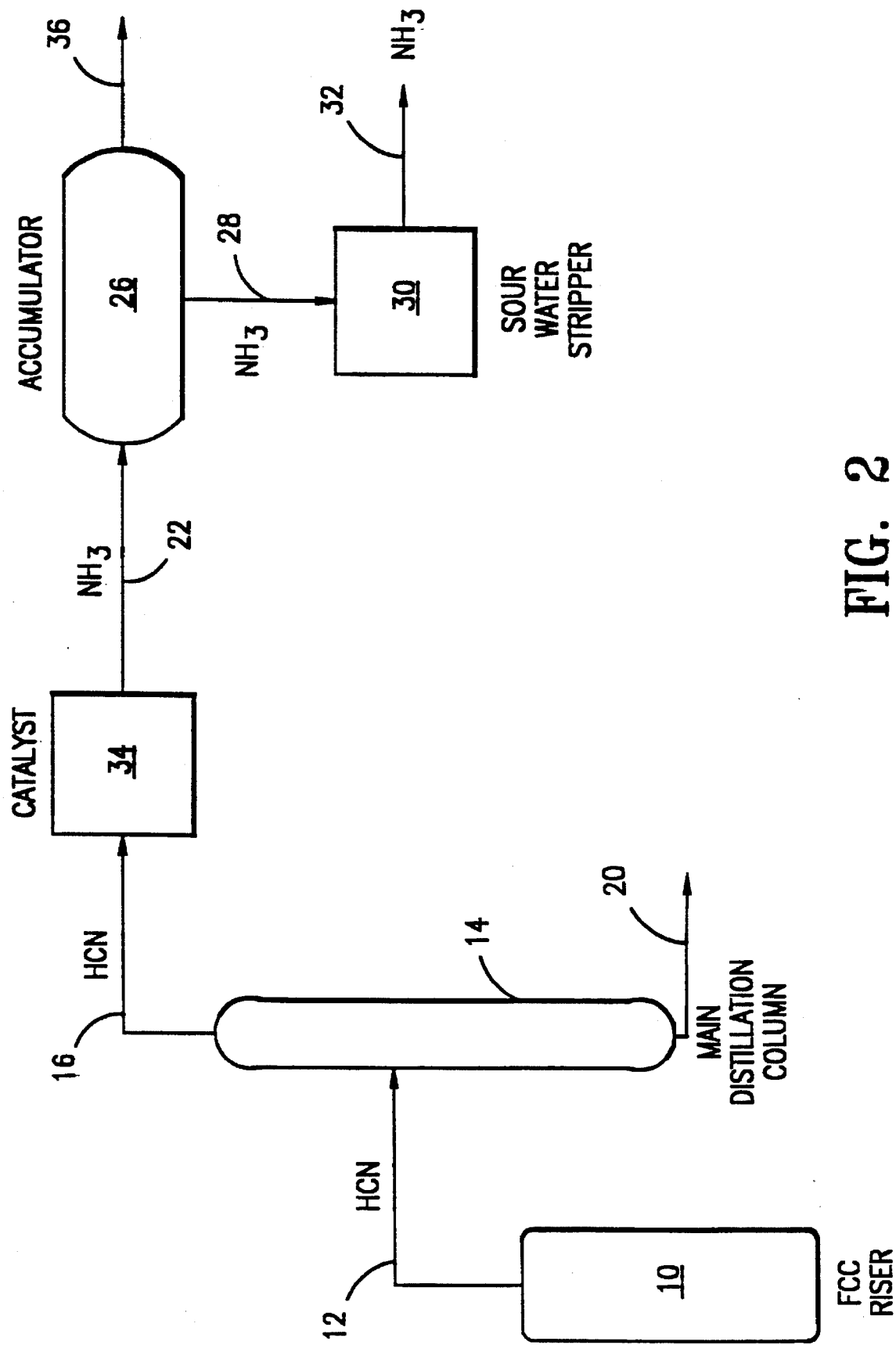
FIG. 2 is a block diagram of the preferred embodiment of this invention where HCN is converted to $NH_3$ via catalytic hydrolysis.

In a preferred embodiment of this invention, overhead from the FCC riser column and the main distillation column are processed in the conventional manner. However, water wash 18 is replaced by reactor 34 as is depicted in FIG. 2. Reactor 34 contains a bed for the removal of HCN. The material in the bed is comprised of catalyst which is selected from a member of the group consisting of $MgO/SiO_2$, $SnO_2$, $Li_2O$, and vanadia/titania. Hydrocarbonaceous gas containing HCN is allowed to remain in contact with said catalyst under conditions and for a time sufficient to convert HCN to $NH_3$ while avoiding degradation or polymerization of olefinic hydrocarbons contained in said gas stream. The preferred operating conditions are a space velocity of about 100 to about 100,000 $hr^{-1}$ and the temperature is from about 150° to about 500° C. Water vapor entrained in the hydrocarbonaceous gas will generally be sufficient to accomplish the required conversion of HCN to $NH_3$. If additional water is required it can be added to the reactor in the form of steam to obtain the desired conversion. The conversion process is monitored to remove HCN impurities from the gaseous process stream at commercially practical temperatures and space velocities to the desired low concentrations.

Since the gas stream containing HCN contains other species of commercial value, e.g. $C_1$ to $C_4$ hydrocarbons, the catalyst composition and operating conditions are controlled so that these species are not degraded by the catalyst. For example, strong acid sites on the catalyst may need to be neutralized to prevent polymerization of olefinic compounds such as propenes and butenes, or the temperature of operation may need to be limited to prevent oxidation of hydrocarbons.

The conversion of a gaseous stream in accordance with this invention is intended to encompass a fixed bed operation as well as the use of a moving or fluidized absorbent bed. The particular method of contacting the gaseous stream with the adsorbent is not critical for purposes of this invention.

The removal of impurities other than HCN that exit from the gaseous stream may be advantageously carried out in a primary purification step using regenerable liquid adsorbents which are known in the art. Thus, for example, gaseous sulfur compounds, such as $H_2S$ and $SO_2$ may be suitably removed from the process stream prior to removal of HCN using a liquid solution of ethanol-amines or alkali hydroxides. Similarly, a portion of the HCN in the process stream may be initially removed by the aforementioned adsorbents or in an ammonia solution prior to reducing the HCN content to the desired final concentrations in accordance with the present invention.

Hydrocarbonaceous gas emitted from reactor 34 via conduit 22 is monitored to maintain a desired level of HCN removal and $NH_3$ conversion. This converted gas stream is afterwards directed into accumulator 26. In accumulator 26 additional entrained water containing $NH_3$ is separated from the gas. Substantially water and HCN free gas is removed from the accumulator by conduit 36. Separated $NH_3$ and water from the accumulator are removed therefrom by conduit 28 into sour water stripper 30. Substantially $CN^-$ free gas from accumulator 26 is utilized in the refinery operations or flared. Substantially $CN^-$ free water containing $NH_3$ ions is removed from sour water stripper 30 via conduit 32 and sent to a disposal unit for facilitated disposal since the cyanide concentration therein has been reduced to environmentally acceptable levels.

In order to demonstrate the efficacy of this novel process, tests were run on HCN containing streams over the catalysts of this invention.

| Catalyst | Temp. (°C.) | ppm inlet HCN | ppm exit HCN | ppm exit NH$_3$ |
|---|---|---|---|---|
| MgO/SiO$_2$ | 400 | 100 | 0 | 100 |
| SnO$_2$ | 500 | 100 | 2 | 82 |
| Li$_2$O/SiO$_2$ | 500 | 100 | 21 | 70 |

Obviously, many other variations and modifications of this invention as previously set forth may be made without departing from the spirit and scope of this invention as those skilled in the art readily understand. Such variations and modifications are considered part of this invention and within the purview and scope of the appended claims.

What is claimed is:

1. A process for removing HCN from a hydrocarbonaceous gas stream comprising:
   a) contacting a hydrocarbonaceous gas stream containing HCN with a catalyst selected from a member of the group consisting of MgO/SiO$_2$, SnO$_2$, Li$_2$O, and vanadia/titania in the presence of water;
   b) allowing said gas to remain in contact with said catalyst under conditions and for a time sufficient to convert HCN to NH$_3$ while avoiding degradation or polymerization of olefinic hydrocarbons contained in said gas stream; and
   c) separating said NH$_3$ and water from the hydrocarbonaceous gas stream substantially devoid of HCN.

2. The process as recited in claim 1 where the gas stream is derived as overhead from a main distillation column fluidly connected to overhead from a FCC riser column.

3. The process as recited in claim 1 where said gas stream comprises C$_1$ to C$_4$ hydrocarbons.

4. The process as recited in claim 1 where vanadia/titania comprises the catalyst, the space velocity is about 100 to about 100,000 hr$^{-1}$ and the temperature is from about 150° to about 500° C.

5. The method as recited in claim 1 where NH$_3$ resultant from step c) is separated by absorption in water.

6. The method as recited in claim 1 where NH$_3$ resultant from step c) is absorbed in water contained in a refinery sour water stripper and where subsequently water from said stripper is mixed with other refinery waste water streams and disposed of.

7. A process for removing HCN from a hydrocarbonaceous gas stream comprising:
   a) contacting a hydrocarbonaceous gas stream containing HCN with a vanadia/titania catalyst in the presence of water;
   b) allowing said gas to remain in contact with said catalyst under conditions and for a time sufficient to convert HCN to NH$_3$ while avoiding degradation or polymerization of olefinic hydrocarbons contained in said gas stream; and
   c) separating said NH$_3$ and water from the hydrocarbonaceous gas stream substantially devoid of HCN.

8. The process as recited in claim 7 where the gas stream is derived as overhead from a main distillation column fluidly connected to overhead from a FCC riser column.

9. The process as recited in claim 7 where said gas stream comprises C$_1$ to C$_4$ hydrocarbons.

10. The process as recited in claim 7 where the space velocity is about 100 to about 100,000 hr$^{-1}$ and the temperature is from about 150° to about 500° C.

11. The process as recited in claim 7 where NH$_3$ resultant from step c) is separated by absorption in water.

12. The process as recited in claim 7 where NH$_3$ resultant from step c) is absorbed in water contained in a refinery sour water stripper and where subsequently water from said stripper is mixed with other refinery waste water streams and disposed of.

13. A process for removing HCN from a hydrocarbonaceous gas stream comprising:
   a) contacting a hydrocarbonaceous gas stream containing HCN with a catalyst selected from a member of the group consisting of MgO/SiO$_2$, SnO$_2$, Li$_2$O, and vanadia/titania in the presence of water;
   b) allowing said gas to remain in contact with said catalyst under a space velocity of about 100 to about 100,000 hr$^{-1}$ and a temperature of from about 150° to about 500° C. and for a time sufficient to convert HCN to NH$_3$ while avoiding degradation or polymerization of olefinic hydrocarbons contained in said gas stream; and
   c) separating said NH$_3$ and water from the hydrocarbonaceous gas stream substantially devoid of HCN.

14. The process as recited in claim 1 where gaseous sulfur compounds are removed from the hydrocarbonaceous gas stream prior to removing HCN via a liquid solution of ethanol-amine or an alkali hydroxide.

15. The process as recited in claim 1 where a portion of HCN is removed from the hydrocarbonaceous gas stream via a liquid solution of ethanol-amine, an alkali hydroxide, or ammonia prior to reducing the HCN content to a desired final concentration.

16. The process as recited in claim 1 where in step c) the hydrocarbonaceous gas stream is monitored to maintain a desired level of HCN removal and NH$_3$ conversion.

17. The process as recited in claim 1 where the catalyst is contained in a fixed bed.

18. The process as recited in claim 1 where the catalyst is contained in a moving or fluidized absorbent bed.

19. The process as recited in claim 1 where in step c) the hydrocarbonaceous gas stream is utilized in refinery operations or flared.

20. A process for removing HCN from a hydrocarbonaceous gas stream comprising:
   a) contacting a hydrocarbonaceous gas stream containing HCN with a catalyst selected from a member of the group consisting of SnO$_2$ and Li$_2$O in the presence of water;
   b) allowing said gas to remain in contact with said catalyst under conditions and for a time sufficient to convert HCN to NH$_3$ while avoiding degradation or polymerization of olefinic hydrocarbons contained in said gas stream; and
   c) separating said NH$_3$ and water from the hydrocarbonaceous gas stream substantially devoid of HCN.

* * * * *